(12) United States Patent
Venkatraman et al.

(10) Patent No.: US 9,392,417 B1
(45) Date of Patent: Jul. 12, 2016

(54) MANAGING ACTIVITIES PERFORMED BY A PLURALITY OF COLLOCATED MOBILE DEVICES

(71) Applicant: QUALCOMM Incorporated, San Diego, CA (US)

(72) Inventors: Sai Pradeep Venkatraman, Santa Clara, CA (US); Benjamin Alfred Werner, Santa Clara, CA (US); Weihua Gao, San Jose, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 14/636,878

(22) Filed: Mar. 3, 2015

(51) Int. Cl.
*H04W 84/20* (2009.01)
*H04W 88/02* (2009.01)
*H04W 4/02* (2009.01)
*H04W 4/00* (2009.01)
*H04B 1/3827* (2015.01)

(52) U.S. Cl.
CPC .............. *H04W 4/028* (2013.01); *H04B 1/385* (2013.01); *H04W 4/001* (2013.01); *H04W 84/20* (2013.01); *H04W 88/02* (2013.01)

(58) Field of Classification Search
CPC ....... H04W 4/02; H04W 64/00; H04W 84/20; H04W 88/02; H04W 4/001; H04W 4/028; H04L 29/08657; H04L 29/08108; H04L 29/08936
See application file for complete search history.

(56) References Cited

U.S. PATENT DOCUMENTS

| 5,594,951 A | 1/1997 | Bellin |
| 5,604,708 A | 2/1997 | Helms et al. |
| 5,714,870 A | 2/1998 | Dunstan |
| 5,848,364 A | 12/1998 | Ohashi |
| 5,883,594 A | 3/1999 | Lau |
| 5,947,775 A | 9/1999 | Yamamoto et al. |

(Continued)

FOREIGN PATENT DOCUMENTS

| DE | 102011081402 A1 | 2/2013 |
| EP | 2046087 A1 | 4/2009 |

(Continued)

OTHER PUBLICATIONS

Kong J., et al., "Ubiquitous Interacting Object: A Distributed and Localized Approach to Building Ubiquitous Computing Applications," ACM Transactions on Interactive Intelligent Systems, 2013, pp. 1-25.

(Continued)

*Primary Examiner* — Ted Wang
(74) *Attorney, Agent, or Firm* — Muncy, Geissler, Olds & Lowe, P.C.

(57) ABSTRACT

Systems and methods for managing activities among collocated mobile devices are disclosed. A controller determines a route of travel corresponding to two or more collocated mobile devices prior to a start of travel, and a set of activities to be performed by the two or more collocated mobile devices after the start of travel based, at least in part, on the route of travel. At least a portion of the set of activities is assigned to a first set of subsystems in a first mobile device and a second set of subsystems in a second mobile device of the two or more collocated mobile devices, wherein the first mobile device and the second mobile device are configured to communicate with one another, and the first set of subsystems and the second set of subsystems have at least one subsystem which is different.

30 Claims, 5 Drawing Sheets

(56) References Cited

U.S. PATENT DOCUMENTS

| | | |
|---|---|---|
| 5,953,677 A | 9/1999 | Sato |
| 6,097,958 A | 8/2000 | Bergen |
| 6,408,196 B2 | 6/2002 | Sheynblat et al. |
| 6,710,578 B1 | 3/2004 | Sklovsky |
| 7,057,372 B2 | 6/2006 | Chen et al. |
| 7,271,765 B2 | 9/2007 | Stilp et al. |
| 7,359,713 B1 | 4/2008 | Tiwari |
| 7,783,302 B2 | 8/2010 | Hupp et al. |
| 7,848,270 B2 | 12/2010 | Hilmersson |
| 7,873,349 B1 | 1/2011 | Smith et al. |
| 7,953,459 B2 | 5/2011 | Kim et al. |
| 8,060,108 B1 | 11/2011 | Rayburn et al. |
| 8,072,379 B2 | 12/2011 | Gopinath |
| 8,195,468 B2 | 6/2012 | Weider et al. |
| 8,214,139 B2 | 7/2012 | Yonker et al. |
| 8,214,910 B1 | 7/2012 | Gossweiler, III et al. |
| 8,228,234 B2 | 7/2012 | Fong et al. |
| 8,472,973 B2 | 6/2013 | Lin et al. |
| 8,744,804 B2 | 6/2014 | Messenger et al. |
| 2001/0041960 A1 | 11/2001 | Hashida |
| 2003/0104849 A1 | 6/2003 | Arimitsu |
| 2004/0192330 A1 | 9/2004 | Gaal |
| 2004/0198386 A1 | 10/2004 | Dupray |
| 2005/0037775 A1 | 2/2005 | Moeglein et al. |
| 2005/0060088 A1 | 3/2005 | Helal et al. |
| 2005/0130677 A1 | 6/2005 | Meunier et al. |
| 2006/0125644 A1 | 6/2006 | Sharp |
| 2006/0255963 A1 | 11/2006 | Thompson et al. |
| 2007/0037610 A1 | 2/2007 | Logan |
| 2007/0089065 A1 | 4/2007 | Lane et al. |
| 2007/0178913 A1 | 8/2007 | Niemenmaa et al. |
| 2008/0162034 A1 | 7/2008 | Breen |
| 2009/0143018 A1 | 6/2009 | Anderson et al. |
| 2009/0164115 A1 | 6/2009 | Kosakowski et al. |
| 2009/0164120 A1 | 6/2009 | Boore et al. |
| 2009/0213004 A1 | 8/2009 | Rhodes et al. |
| 2009/0216438 A1 | 8/2009 | Shafer |
| 2009/0286549 A1 | 11/2009 | Canon et al. |
| 2010/0069062 A1 | 3/2010 | Horn et al. |
| 2010/0087230 A1 | 4/2010 | Peh et al. |
| 2010/0106603 A1 | 4/2010 | Dey et al. |
| 2010/0161831 A1 | 6/2010 | Haas et al. |
| 2010/0197321 A1 | 8/2010 | Kim et al. |
| 2010/0240391 A1 | 9/2010 | Povey |
| 2010/0241496 A1 | 9/2010 | Gupta et al. |
| 2011/0172906 A1 | 7/2011 | Das et al. |
| 2011/0177809 A1 | 7/2011 | Pakzad et al. |
| 2011/0178701 A1 | 7/2011 | Gupta et al. |
| 2011/0239026 A1 | 9/2011 | Kulik |
| 2011/0250871 A1 | 10/2011 | Huang et al. |
| 2011/0307891 A1 | 12/2011 | Orr et al. |
| 2012/0064922 A1 | 3/2012 | Podoloff et al. |
| 2012/0100895 A1 | 4/2012 | Priyantha et al. |
| 2012/0130632 A1 | 5/2012 | Bandyopadhyay et al. |
| 2012/0136529 A1* | 5/2012 | Curtis ................ G01C 21/20 701/32.2 |
| 2012/0143495 A1 | 6/2012 | Dantu |
| 2012/0157113 A1 | 6/2012 | Brisebois et al. |
| 2012/0176525 A1 | 7/2012 | Garin et al. |
| 2012/0203453 A1 | 8/2012 | Lundquist et al. |
| 2012/0268249 A1 | 10/2012 | Kansal et al. |
| 2013/0017840 A1 | 1/2013 | Moeglein et al. |
| 2013/0158860 A1 | 6/2013 | Gum |
| 2013/0297220 A1* | 11/2013 | Yuen ................ A61B 5/0002 702/19 |
| 2014/0087711 A1 | 3/2014 | Geyer et al. |
| 2014/0106677 A1 | 4/2014 | Altman |
| 2014/0107919 A1* | 4/2014 | Venkatraman ......... G01S 19/48 701/466 |
| 2014/0129175 A1 | 5/2014 | Poduri et al. |

FOREIGN PATENT DOCUMENTS

| | | |
|---|---|---|
| EP | 2270535 A2 | 1/2011 |
| EP | 2648389 A1 | 10/2013 |
| JP | 9005102 A | 1/1997 |
| WO | 2010025467 A1 | 3/2010 |
| WO | 2011107652 A1 | 9/2011 |
| WO | 2012001215 A1 | 1/2012 |

OTHER PUBLICATIONS

International Search Report and Written Opinion—PCT/US2016/017105—ISA/EPO—Apr. 20, 2016.

* cited by examiner

402
Determine a route of travel corresponding to two or more collocated mobile devices prior to a start of travel

404
Determine a set of activities to be performed by the two or more collocated mobile devices after the start of travel based, at least in part, on the route of travel

406
Assign at least a portion of the activities among a first set of subsystems in a first mobile device and a second set of subsystems in a second mobile device of the two or more collocated mobile devices,
wherein the first mobile device and the second mobile device are configured to communicate with one another, wherein the first set of subsystems and the second set of subsystems have at least one subsystem which is different

MANAGING ACTIVITIES PERFORMED BY A PLURALITY OF COLLOCATED MOBILE DEVICES

FIELD OF DISCLOSURE

Disclosed aspects relate to data processing techniques for use in a plurality of mobile devices that may be collocated (e.g., nearby one another), and in particular to data processing techniques for use in managing activities among two or more mobile devices, wherein the activities may be associated with one or more positioning functions.

BACKGROUND

The growing popularity of wearable electronic devices like smart watches, wristbands or arm bands, anklets or leg bands, hats, shoes, belts, vests, eye glasses, goggles, badges, rings, etc., has led to some users having multiple mobile devices (which may be considered "collocated" as being proximate or nearby one another), such as, for example being carried on their person. As such, in certain instances a user may carry multiple mobile devices such as a smart-phone and a smart-watch, which may be equipped with various functionalities. For example, in certain instances, two or more such collocated mobile devices may be equipped with positioning related functionality, e.g., for various navigation, tracking, routing, and/or other like capabilities. Hence, in certain instances, two or more of such collocated mobile devices may include various components or subsystems, such as sensors, functional blocks, communication modules, etc., that may provide or otherwise support positioning.

With respect to positioning, for example, different mobile devices and their component sets of subsystems may be capable of performing some of the same or related activities for navigating and/or tracking a user along a desired route and providing related metrics such as speed, elevation, calories burned, etc. Thus, it may be that two or more mobile devices may consume power to perform the same or similar functions. Since mobile devices tend to rely heavily on battery power, it is usually desirable to reduce power consumption and increase battery life.

SUMMARY

Exemplary embodiments are directed to systems and methods for managing activities among collocated mobile devices are disclosed. In exemplary aspects, a controller determines a route of travel corresponding to two or more collocated mobile devices prior to a start of travel, and a set of activities to be performed by the two or more collocated mobile devices after the start of travel based, at least in part, on the route of travel. At least a portion of the set of activities is assigned to a first set of subsystems in a first mobile device and a second set of subsystems in a second mobile device of the two or more collocated mobile devices, wherein the first mobile device and the second mobile device are configured to communicate with one another, and the first set of subsystems and the second set of subsystems have at least one subsystem which is different. In some cases where there are changes in pre-planned conditions, such as changes to the route of travel (e.g., a new route of travel, changes in environmental conditions, or changes in speed or velocity along the route of travel, etc.) and/or conditions of one or more of the collocated devices (e.g., battery level, activity level, or availability of the at least one of the two or more collocated mobile devices, etc.) these changes are detected and a new or revised set of activities are generated by the controller, for example, based on the changes and assigned to the collocated mobile devices accordingly.

For example, an exemplary aspect pertains to a method for use in managing activities among two or more collocated mobile devices, the method comprising: determining a route of travel corresponding to the two or more collocated mobile devices prior to a start of travel, determining a set of activities to be performed by the two or more collocated mobile devices after the start of travel based, at least in part, on the route of travel, and assigning at least a portion of the set of activities among a first set of subsystems in a first mobile device of the two or more collocated mobile devices and a second set of subsystems in a second mobile device of the two or more collocated mobile devices. The first mobile device and the second mobile device are configured to communicate with one another, and the first set of subsystems and the second set of subsystems have at least one subsystem which is different.

Another exemplary aspect relates to an apparatus configured to manage activities among two or more collocated mobile devices. The apparatus comprises memory and a processor coupled to the memory. The processor is configured to: determine a route of travel corresponding to the two or more collocated mobile devices prior to a start of travel, determine a set of activities to be performed by the two or more collocated mobile devices after the start of travel based, at least in part, on the route of travel, and assign at least a portion of the set of activities among a first set of subsystems in a first mobile device of the two or more collocated mobile devices and a second set of subsystems in a second mobile device of the two or more collocated mobile devices. The first mobile device and the second mobile device are configured to communicate with one another, and the first set of subsystems and the second set of subsystems have at least one subsystem which is different.

Another exemplary aspect relates to a system for use in managing activities among two or more collocated mobile devices. The system comprises means for determining a route of travel corresponding to the two or more collocated mobile devices prior to a start of travel, means for determining a set of activities to be performed by the two or more collocated mobile devices after the start of travel based, at least in part, on the route of travel, and means for assigning at least a portion of the set of activities among a first set of subsystems in a first mobile device of the two or more collocated mobile devices and a second set of subsystems in a second mobile device of the two or more collocated mobile devices. The first mobile device and the second mobile device are configured to communicate with one another, and the first set of subsystems and the second set of subsystems have at least one subsystem which is different.

Yet another exemplary aspect relates to an article for use in managing activities among two or more collocated mobile devices. The article comprises a non-transitory computer-readable storage medium having stored therein instructions that are executable by a processor to: determine a route of travel corresponding to the two or more collocated mobile devices prior to a start of travel, determine a set of activities to be performed by the two or more collocated mobile devices after the start of travel based, at least in part, on the route of travel, and assign at least a portion of the set of activities among a first set of subsystems in a first mobile device of the two or more collocated mobile devices and a second set of subsystems in a second mobile device of the two or more collocated mobile devices. The first mobile device and the second mobile device are configured to communicate with one another, and the first set of subsystems and the second set of subsystems have at least one subsystem which is different.

BRIEF DESCRIPTION OF THE DRAWINGS

The accompanying drawings are presented to aid in the description of embodiments of the disclosure and are provided solely for illustration of the embodiments and not limitation thereof.

DETAILED DESCRIPTION

Systems and methods for managing activities (e.g., tasks, capabilities, components, subsystems, etc.) among two or more mobile devices located nearby one another, such as, for example, on a user's person, among or nearby a group of people, wherein one or more may be part of a machine or vehicle nearby one or more mobile devices on a person or group, just to name a few examples, are disclosed. An aspect determines a route of travel for the user prior to a start of travel (e.g., such a route of travel may correspond to a planned or predicted route of travel, or otherwise estimated or likely heading or trajectory, etc.), determines a set of activities associated with the route, and schedules the set of activities among a first set of subsystems in a first mobile device of the two or more mobile devices and a second set of subsystems in a second mobile device of the two or more mobile devices. In certain implementations, the first mobile device and the second mobile device may be configured to communicate with one another directly or indirectly (e.g., via one or more other devices). In certain instances, the first set of subsystems and the second set of subsystems may have at least one subsystem which is different.

These and other aspects of the disclosure are disclosed in the following description and related drawings directed to specific embodiments of the disclosure. Alternate embodiments may be devised without departing from the scope of the disclosure. Additionally, well-known elements of the disclosure will not be described in detail or will be omitted so as not to obscure the relevant details of the disclosure.

The word "exemplary" is used herein to mean "serving as an example, instance, or illustration." Any embodiment described herein as "exemplary" is not necessarily to be construed as preferred or advantageous over other embodiments. Likewise, the term "embodiments of the disclosure" does not require that all embodiments of the disclosure include the discussed feature, advantage or mode of operation.

The terminology used herein is for the purpose of describing particular embodiments only and is not intended to be limiting of embodiments of the disclosure. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

Further, many embodiments are described in terms of sequences of actions to be performed by, for example, elements of a computing device. It will be recognized that various actions described herein can be performed by specific circuits (e.g., application specific integrated circuits (ASICs)), by program instructions being executed by one or more processors, or by a combination of both. Additionally, these sequence of actions described herein can be considered to be embodied entirely within any form of computer readable storage medium having stored therein a corresponding set of computer instructions that upon execution would cause an associated processor to perform the functionality described herein. Thus, the various aspects of the disclosure may be embodied in a number of different forms, all of which have been contemplated to be within the scope of the claimed subject matter. In addition, for each of the embodiments described herein, the corresponding form of any such embodiments may be described herein as, for example, "logic configured to" perform the described action.

Exemplary aspects relate to a controller or manager configured to manage a set of activities among two or more devices. More specifically, the activities may relate to various positioning functions, applications, and/or capabilities. For example, an aspect may relate to a controller configured to manage a set of activities between a first device (e.g., smart-phone, lap-top, etc.) and a second device (e.g. smart-watch, smart-phone, navigation device, etc.), which may each have a respective set of subsystems/components integrated or otherwise provisioned therein. For example, these subsystems/components may include one or more sensors, one or more communication modules, one or more processing systems, etc., one or more of which may be used to provide or support positioning. By managing activities on the smart-phone and smart-watch in a collaborative manner, allocation and/or usage of resources may be better optimized, performance may be improved, and redundant processing may be reduced, avoided, or otherwise controlled. For example, by allocating a set of activities to be performed on a first set of subsystems of the smart-phone (first device) and avoiding repetitive performance of the same or related activities on a second set of subsystems of the smart-watch (second device), the subsystems of the smart-watch may be disabled or powered down (e.g., in order to reduce power consumption). Accordingly, assigning or allocating at least one activity among the first and set of subsystems may involve disabling one or more subsystems in the first set of subsystems, disabling one or more subsystems in the second set of subsystems, or both. Further, some mobile devices may be configured with subsystems which have different specifications, and thus, a controller may be able to select among available subsystems across the two or more devices, for a particular activity. In this manner, performance may be improved.

An exemplary controller may include systems, devices, methods, and other implementations to predictively determine a set of activities to be performed for a particular function, application, and/or capability. For the case of a positioning application, some of these activities may comprise activities to be performed along a route of travel (e.g., for a person carrying the mobile devices or otherwise being transported along with the mobile devices). Such activities include, for example, activating or deactivating certain subsystems such as sensors or receivers depending on where a mobile device is, obtaining map information for a particular area in which a mobile device will be traveling prior to arriving at that area, etc. For example, a pressure sensor (e.g., a barometer) may not be needed if a route of travel is expected to remain on a level surface or same altitude, e.g., one level of a building. In another example, a GNSS receiver may not be needed when a route of travel is expected to remain indoors. In another example, when a mobile device transitions from an indoor to an outdoor environment, certain positioning modules may be configured to obtain additional assistance data for positioning, possibly while the mobile device is still indoors. Thus, some positioning activities may require particular subsystems or components, and accordingly, the related subsystems or components may be turned on or off or otherwise affected in some manner depending on whether or not the corresponding activity is allocated or assigned to an applicable mobile device by the controller.

Additionally in the case of some functions/capabilities which may involve routing or navigational features, activities other than those specifically related to positioning may be performed. For example, some health and fitness related capabilities may involve biometric functions such as heart rate monitoring, pulse rate monitoring, etc. Such activities may be associated with positioning to provide a user of the mobile device(s) with biometric measurements on the fly during a user's fitness activity (e.g., running, swimming, cycling, etc.) and/or a record of these measurements for goal tracking and future analysis.

Thus, in this disclosure, a set of exemplary activities related to positioning functions collectively refers to any such routing activities, navigation activities, location activities, biometric functions, etc., which may be performed in conjunction with tracking a user's progress along a route or providing navigational assistance or other useful information to a user. In exemplary aspects, these activities may be scheduled, assigned, or performed in a collaborative and/or distributed manner among two or more mobile devices by a controller, which may improve overall performance and minimize power consumed during the execution of the activities.

As such, managing of exemplary activities can involve a enabling and/or disabling of one or more subsystems or components of sets of subsystems that may be included on one or more of the two or more devices. These subsystems may include sensors (e.g., positioning sensors, accelerometers, gyroscopes, magnetometers, pressure sensors, etc.,), application specific processors, digital signal processors, general purpose processors, memory systems, display systems, communication systems including antennae, receivers, transmitters, monitors such as heart rate monitors, blood pressure monitors, etc., just to name a few examples. In some implementations, an exemplary controller (which may be operating in whole or part in at least one of the two or more mobile devices, and/or in one or more separate remote computing devices) may be configured to generate or create a list or set of activities to be performed on these various subsystems. Each device may have its own unique set of subsystems integrated thereon, and moreover, similar subsystems on each mobile device may have different specifications. In exemplary aspects, the controller may generate a set of activities in the form of a list, a schedule, a plan etc., which may be based on a particular route of travel and subsystems present across the two or more mobile devices. The controller may also be aware of which subsystems may be available for to schedule, assign, and/or manage activities on, and which subsystems may be unavailable (e.g., because they may be required by other applications which may be running on the mobile devices).

Exemplary aspects may be particularly applied to cases where the two or more mobile devices have at least one subsystem or component which is different or not common. Example aspects relate to cases where one mobile device is a smart-phone, tablet, personal device assistant (PDA), etc., which may be used for multimedia and computation applications, and another mobile device is a wearable electronic device such as a smart-watch. Thus, these two devices may have some similar subsystems whereas there are likely to be differences based on the different uses and requirements of these mobile devices. Moreover, in exemplary aspects, the two or more mobile devices may be on a user's person or in their presence, which may indicate that the mobile devices are in close proximity to one another and thus may be considered to be collocated at a same position. Thus, collaborative scheduling of activities along a route of travel may be possible across these two or more mobile devices.

In some aspects, two or more mobile devices may be collocated even if they are not on the person, or under control of, or operated by, a single user. For example, two or more collocated mobile devices in this disclosure may be within close proximity of one another and may pertain to one or more persons and/or objects. In an example scenario, a first mobile device (e.g., a smart-phone) may be carried by a first user and a second mobile device (e.g., another smart-phone, a smart-watch, or a lap-top) may be carried by a second user, where the first and second user are known to share a common route of travel whilst being in close proximity of one another, such as, traveling in a same automobile or walking together along a same path. In such a scenario, the first and second mobile devices may be treated as collocated devices and a controller may manage activities among the two mobile devices in a collaborative manner. In another scenario, a user carrying a smart-phone may travel in an automobile equipped with a navigation system, where the user's smart-phone and the automobile's navigation system may be treated as collocated devices for collaborative management and control of activities to be performed. For example, positioning activities for navigating through a route of travel may be de-activated on the user's smart-phone, since the automobile's navigation system may be capable of performing these activities. In this manner, battery life on the user's smart phone may be conserved.

In exemplary aspects, two or more mobile devices may be determined to be collocated at the time a route of travel and associated activities have been determined. However, in some cases, one or more mobile devices may be discovered along an existing route of travel. For example, if a second user carrying a second mobile device were to join the first user carrying the first mobile device in the automobile equipped with a navigation system in the above example, the second mobile device may be discovered by a controller, whereby the controller may manage activities pertaining to the common route of travel amongst the first mobile device, the second mobile device, and the automobile's navigation system.

Accordingly, while a detailed discussion of collocated mobile devices will be provided for cases where two or more mobile devices are on a same user's person or presence, it will be understood that activities can be controlled and managed for a common route of travel on different types of collocated mobile devices which need not be present on a single user.

Figure 1:
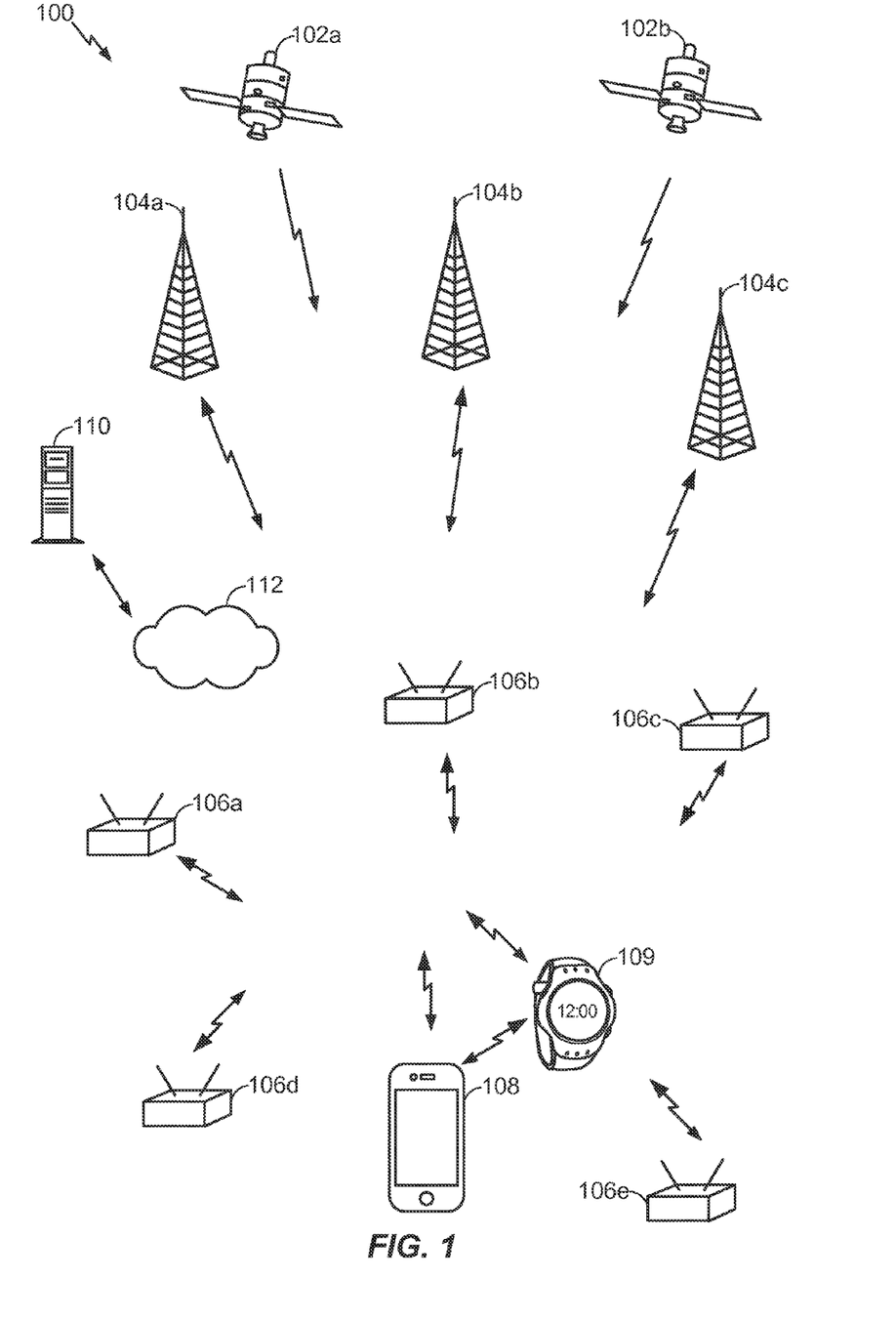
FIG. 1 is a schematic diagram of an example system that includes two or more mobile devices that are located in close proximity to or otherwise nearby one another, in accordance with certain example implementations.

With reference to FIG. 1, a schematic diagram of an example system 100 and various environments in which mobile devices 108 and 109 (which may be collocated) operate is shown. The mobile devices (also referred to as wireless devices or as mobile stations) may be configured to operate and interact with multiple types of other communication systems/devices, including local area network devices (or nodes), such as WLAN for indoor communication, femtocells, Bluetooth-based transceivers, and other types of communication network nodes, wide area wireless network nodes, satellite communication systems, etc., and as such the mobile devices 108 and 109 may include one or more interfaces to communicate with the various types of communications systems. As used herein, communication system/devices with which the mobile devices 108 and 109 may communicate are also referred to as access points (AP's). As used herein, the term "wireless device" may refer to any type of wireless communication device which may transfer information over a network and also have position determination and/or navigation functionality. The mobile devices may be configured as wireless devices, and may include (by way of some non-limiting examples) a cellular mobile terminal, personal communication system (PCS) device, personal navigation device, laptop, personal digital assistant, as well as devices which may be known in the art to include wearable electronic devices, such as, smart-watches, eyeglasses, bracelets, rings, etc., and any other suitable mobile device capable of receiving and processing wireless signals, which may include satellite signals.

In more detail, system 100 may include one or more different types of wireless communication systems and/or wireless positioning systems. Wireless signals from global navigation satellite system (GNSS) sources 102a-b (e.g., satellites) may be used for multi-lateration of mobile devices 108 and 109. One or more terrestrial sources, such as (by way of some non-limiting examples) as cellular base stations, Wide Area Network Wireless Access Points (WAN-WAPs), Wide Area Wireless Network (WWAN), WiMAX (e.g., 802.16), etc. are illustrated as sources 104a-c, which may be used for wireless voice and/or data communication, and as another source of position information for mobile device 108. Sources 104a-c may operate from fixed positions, and provide network coverage over large metropolitan and/or regional areas. One or more other wireless signal sources such as Local Area Network Wireless Access Points (LAN-WAPs), WLAN, Wi-Fi networks (802.11x), cellular piconets and/or femtocells, Bluetooth Networks, etc. (by way of some non-limiting examples), are illustrated as sources 106a-e, which may be used for wireless voice and/or data communication, as well as yet another source for positioning data. Sources 106a-e may operate in environments, that include buildings, and capable of performing communications over smaller geographic regions than a WWAN, for example. Mobile device 108 may derive position information from any one or more of sources 102a-b, 104a-c, and/or 106a-e, in any suitable combination. Furthermore, embodiments can conform to other types of positioning systems that utilize pseudolites or ground-based transceivers. When deriving position, mobile devices 108 and 109 may utilize time of arrival techniques and/or the like, possibly with the assistance of a positioning server 110, which may communicate with mobile device 108 through network 112. Although not illustrated in FIG. 1, it should be understood that some of the terrestrial-based electronic devices (e.g., 104, 110, and 106) may be operatively coupled together via one or more wire/fiber or other like backhaul communication capabilities, possibly including one or more networks and/or other like devices, services, etc.

In FIG. 1, mobile device 108 is representatively shown as a smart-phone and mobile device 109 is representatively shown as a smart-watch, although it will be understood that these representations are merely by way of example, but not limitation. Exemplary aspects are equally applicable to any other set of two or more mobile devices compatible with an example environment such as system 100, and particularly, where the mobile devices are collocated or within close proximity to one another (such as on a user's person, in their clothing, bags, etc.), such that activities may be shared or collaboratively scheduled among these mobile devices. In certain instances, rather than being associated with a person such collocated mobile devices may be associated with another form of an animal, a machine, or some combination thereof. In certain implementations, mobile devices 108 and 109 may also communicate with one another directly or indirectly, for example, via wireless networking technologies such as, Bluetooth connection, WiFi, Ultra Wide Band, Zig-Bee, wireless USB, etc., and/or through any other combination of wireless communication possible within system 100. In some aspects, a wired communication, e.g., through a wire or compatible universal synchronous bus (USB) cable, may also be possible between the mobile devices 108 and 109, particularly where the mobile devices 108 and 109 are collocated or within close proximity to each other, such as on a user's person.

As such, a controller (e.g., integrated on at least one of the mobile devices 108, 109 or on a remote server or other like remote computing device in communication with at least one of the mobile devices 108, 109) may be configured to generate a list or set of activities to be performed based on a predicted or expected route of travel determined for one or both of the mobile devices 108, 109. Such an expected/predicted route of travel may be determined by computing a route between a start and destination point (which may be provided by a user) based on map data available at least one of the mobile devices 108, 109 and/or a remote server (e.g., positioning server 110). In circumstances where more than one route of travel between the start and destination points is possible or available, the selected route of travel may be a route that meets some predetermined criteria (e.g., shortest route, fastest route, etc.). As mentioned, the generated set of activities may pertain to navigation activities, biometric functions, etc., that are to be performed along the route of travel. Further, a schedule may be created for the list of activities, for example, by associating a sequence or time table with the generated list of activities. The schedule of the activities may also be based on a determination that the mobile devices 108 and 109 are approaching or within some proximity to certain points along the route of travel. In some aspects, the controller may be configured to dynamically alter the schedule and/or the list of activities to adapt to changes in the environment and/or the route of travel.

For example, an activity pertaining to activating a GNSS receiver may be associated with a location close to a transition from an indoor to an outdoor environment. Similarly, activities such as obtaining assistance data (including, for example, map data) corresponding to a particular area or region, obtaining assistance data to facilitate a quick fix on satellite signals that may be available within a given region, deactivating a WiFi transceiver, etc., may also be associated with the position of the mobile device(s) being close to a transition from one region to another, possibly with the same or different environments. On the other hand, a position which signifies a transition from an outdoor environment (one type of region)

to an indoor environment (another type of region) may have associated activities such as obtaining radio signal strength and/or propagation time heat maps for one or more WiFi access points pertaining corresponding ranges for the indoor area or particular region therein, floor maps, access point related parameters such as processing gain, transmit power, RTT turnaround calibration functions, etc. Further, activities related to activating or deactivating monitors and sensors used for biometric functions may be associated with particular expected positions, such as position(s) relating to areas with steep or changing elevations (e.g., stairs, an uphill path), different modes of travel (e.g., as may occur in a triathlon), etc.

Figure 2:
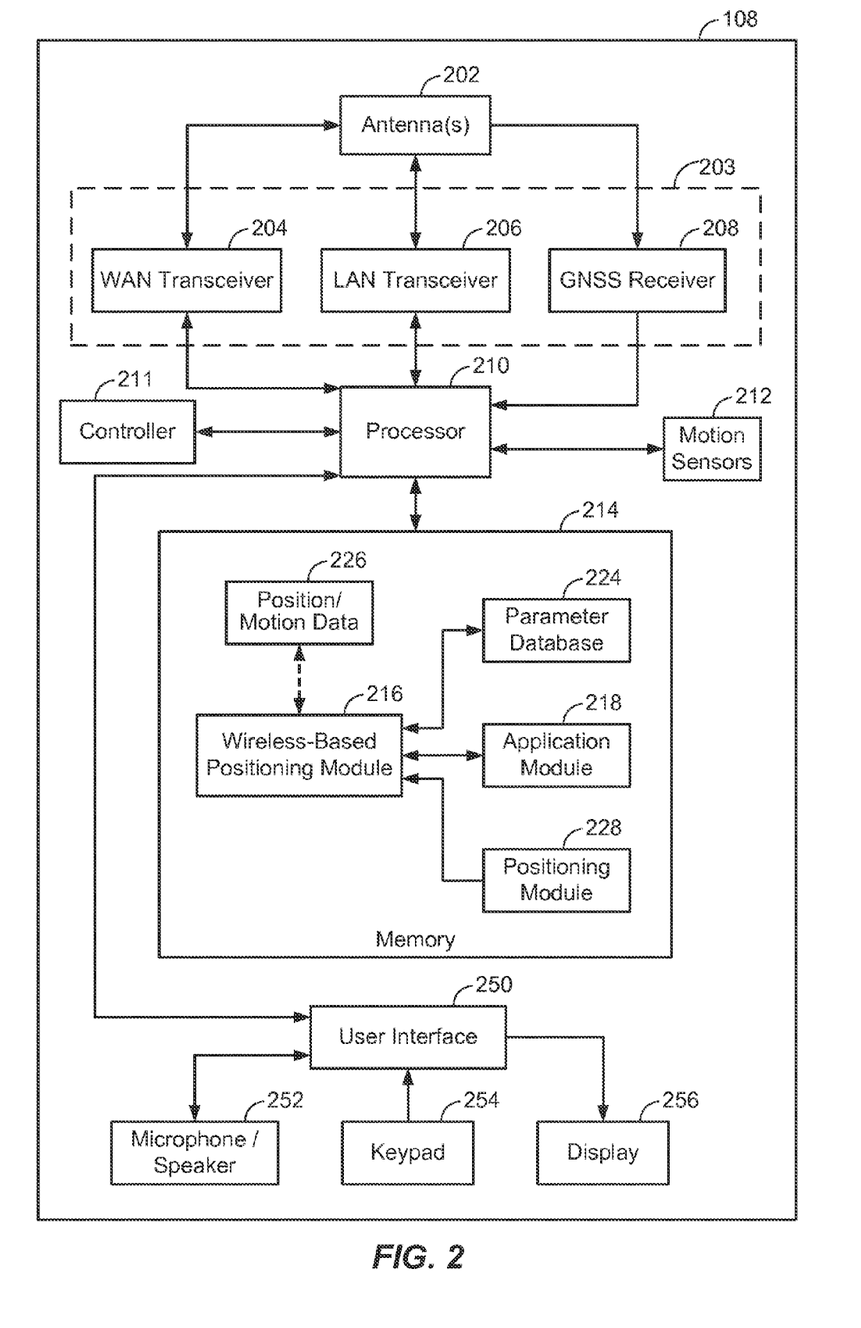
FIG. 2 is a schematic diagram of certain features of a mobile device that may be used in the example system of FIG. 1, in accordance with certain example implementations.

FIG. 2 is a block diagram illustrating various components of an example mobile device 200. Mobile devices 108 and 109 may be configured according to the general framework shown and explained with relation to example mobile device 200, while keeping in mind that each mobile device 108 and 109 may have less, more, or different components in comparison to mobile device 200. In particular embodiments, mobile devices 108 and 109 may have at least one component which is different from one another.

Wide area network (WAN) transceiver 204 may be connected to one or more antennas 202 for communicating with and/or detecting signals to/from sources 104a-c. Wireless local area network (WLAN) transceiver 206 may be connected to one or more antennas 202 for communicating with and/or detecting signals to/from sources 106a-e. GNSS receiver 208 may be connected to the one or more antennas 202 for receiving satellite signals. While GNSS receiver 208 is shown, mobile device 200 may include additional receivers of satellite signals which may be used for positioning. In certain example, implementations, one or more receivers, transmitters, transceivers, and/or the like or some combination thereof may be provided in mobile device 200 (and/or similarly in other electronic devices, computing devices, etc.) as part of a communication interface, which is represented in the example of FIG. 2 by communication interface 203.

Additionally, mobile device 108 may comprise one or more motion sensors 212, which may be coupled to processor 210 to provide movement and/or orientation information which is independent of motion data derived from signals received by WAN transceiver 204, WLAN transceiver 206 and GNSS receiver 208, which are also connected to processor 210. By way of example, motion sensor 212 may utilize motion sensors such as an accelerometer (e.g., a MEMS device), a gyroscope, a geomagnetic sensor (e.g., a compass), an altimeter (e.g., a barometric pressure altimeter), and/or any other type of movement detection sensor. In exemplary embodiments, motion sensor 212 may utilize one or more components or features derived from motion sensors, such as, a pedometer (e.g., as derived from an accelerometer, to detect step counts), and/or a motion classifier or motion mode detector (e.g. to classify/detect motion modes such as stationary, running, driving, etc., which will be discussed further below). Moreover, motion sensor 212 may include a plurality of different types of devices and combine their outputs in order to provide motion information. For example, the motion sensor 212 may use a combination of a multi-axis accelerometer and orientation sensors to provide the ability to compute positions in 2-D and/or 3-D coordinate systems. Processor 210 may include one or more microprocessors, microcontrollers, and/or digital signal processors that provide processing functions, as well as other calculation and control functionality. Processor 210 may be coupled to memory 214, which may include and/or otherwise receive information related to wireless-based positioning module 216, application module 218, positioning module 228, parameter database 224, and position/motion data module 226, whose functions are recognizable by one of ordinary skill in the art, and a detailed description of these will be avoided herein for the sake of brevity.

Processor 210 may include any form of (hardware-based, or a combination of hardware and software based) logic suitable for performing at least the techniques provided herein. For example, processor 210 may be operatively configurable based on instructions in memory 214 to selectively initiate one or more routines that exploit motion data for use in other portions of the mobile device. Mobile device 200 may include user interface module 250 which provides any suitable interface systems, such as microphone/speaker 252, keypad 254, and display 256 that allows user interaction with mobile device 108. Mobile device 200 may be configurable to acquire wireless signals transmitted from, and transmit wireless signals to, one or more wireless communication devices or networks.

Further, as shown, mobile device 200 also includes controller 211 in communication with processor 210, which may include logic configured for managing activities in a collaborative manner with at least one other mobile device. Controller 211 can include logic configured to perform the functions related to managing, scheduling, assigning, etc., for the activities described herein. While controller 211 has been shown as separate from processor 210, the specific functions of controller 211 can also be integrated in processor 210 by suitably enhancing the functionality of processor 210. Further, as previously described, not all instantiations of mobile device 200 (e.g., in mobile devices 108, 109, etc.) require controller 211 to be present, and as such, controller 211 can be present in whole or in part on one or more of the mobile devices, while being able to control or otherwise indicate the managing of activities on one or more other mobile devices. Functionality related to controller 211 may also or alternatively be present in whole or in part on one or more other devices (e.g., one or more remote servers, or other like computing devices, etc.) in some cases. Regardless of the specific implementation, controller 211 may be aware of operational modes/conditions, components, functionalities, and capabilities of each of the one more mobile devices (e.g., mobile devices 108, 109, etc.,) on which activities are to be performed. Controller 211 may obtain information pertaining to location of mobile device 200, readings from sensors and receivers, user inputs, etc., through processor 210 as shown. Controller 211 may also communicate with various components of mobile device 200, as well as the one or more other mobile devices that controller 211 manages, through processor 210. Once again, alternative implementations are possible without deviating from the scope of this disclosure.

According to aspects of this disclosure, each of the various blocks shown in FIG. 2, that constitute mobile device 200, can partially, fully, or in combination with other blocks, constitute a subsystem. Thus, a first mobile device (e.g., mobile device 108) may have a first set of subsystems, and a second mobile device (e.g., mobile device 109) may have a second set of subsystems. Controller 211 can be configured to selectively control, activate, or deactivate one or more subsystems of the first set and the second set for the performance of the generated set of activities. For example, controller 211 may take into account a status of each mobile device (e.g., on, off, sleep, condition, mode, etc.,), statuses of subsystems of each mobile device (e.g., busy, available, already performing a requested activity and can be leveraged, power levels/budgets, etc.), parameters for a desired route-based application, such as a desired level of accuracy in location determination, desired time-to-fix to obtain a GNSS fix, etc., frequency at which results of biometric monitoring or sensor readings need to be obtained, etc. In this manner, controller 211 may manage power usage, reduce redundant processing and potential wastage of power, intelligently schedule and revise schedules for the activities and/or revise the activities themselves, based on the availability and lack thereof of subsystems in the first and second sets, as well as remaining battery life and other real time data related to the first and second mobile devices.

In some aspects, the first mobile device may be a master device and include controller 211 integrated thereon. The second mobile device may be a slave device which performs activities based on instructions or commands received from the master device. In the case where the master device is a mobile phone and the slave device is a smart watch, the two devices may have different sensor capabilities and controller 211 may be aware of the specific capabilities of these two devices. If, for example, the first and second mobile devices are made by a same manufacturer or brand, for example, then controller 211 may be able to obtain specifications of the slave device from the manufacturer. However, there is no such requirement for the first and second mobile devices to share a common brand or manufacturer, as they may be able to communicate specifications through a handshaking mechanism or a link established between them. For example, the slave device may be paired with or tethered to the master device using Bluetooth technology, following which, controller 211 located on the master device may garner required specifications and information of a second set of subsystems located on the slave device through the link. There may be an ongoing communication for obtaining real time information about the status of the various subsystems of the slave device. Controller 211 may be able to perform or coordinate functions for communicating information exchange protocols, rates, formats, etc., as necessary to request and receive the desired information and status messages from the slave device. Some example scenarios will now be described for the collaborative scheduling and management of activities among the first and second mobile devices by controller 211.

Figure 3:
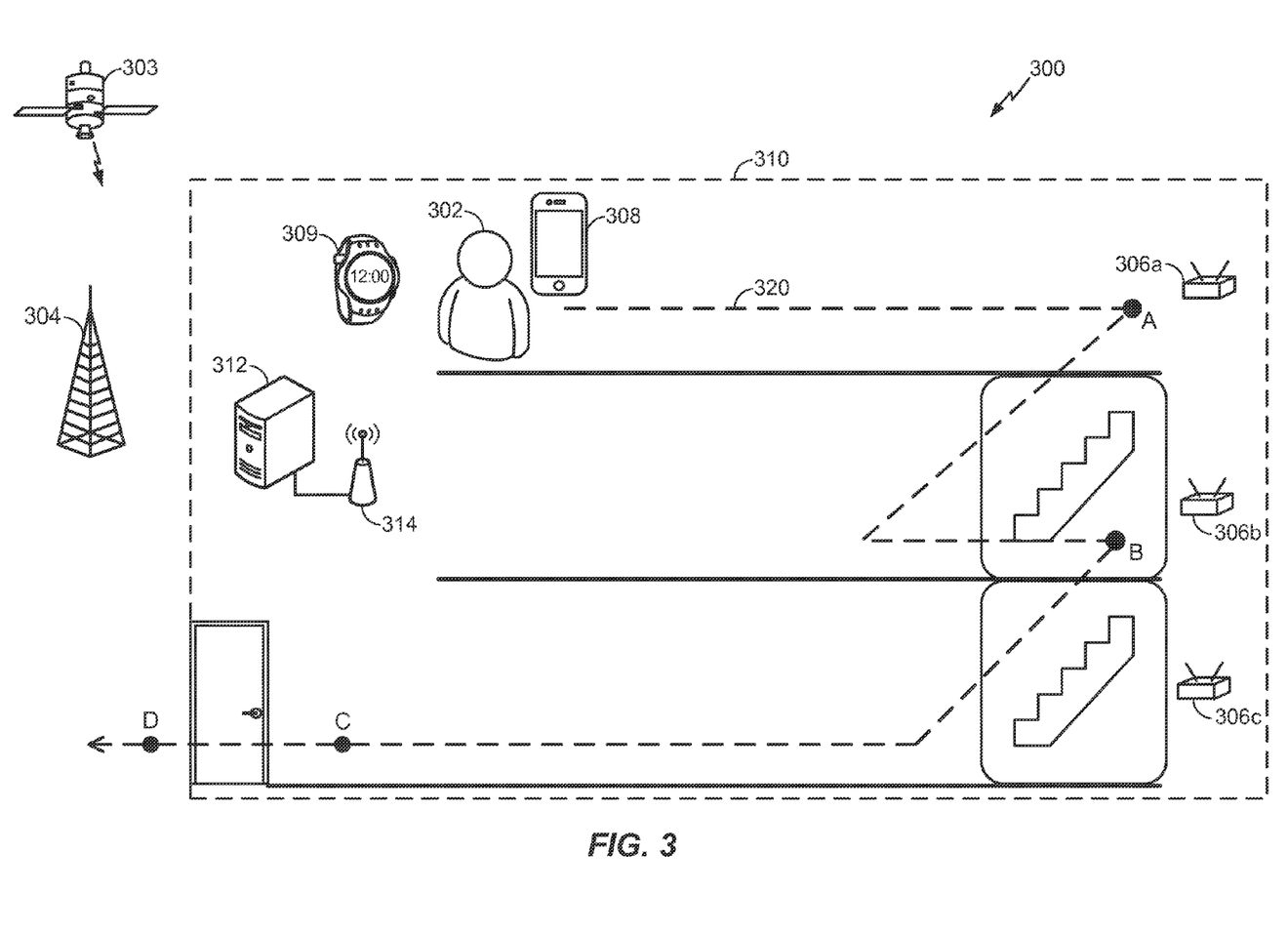
FIG. 3 is a diagram of example indoor/outdoor environments that may correspond to the example system of FIG. 1, within which two or more collocated mobile devices may be moved about together in some manner, in accordance with certain example implementations.

As previously noted, controller 211 may generate a set of activities to be performed for a particular application based on proximity to one or more points along a computed or predetermined route of travel. To illustrate example operations of controller 211, reference is made to FIG. 3, showing a diagram of an example indoor/outdoor environment 300 in which user 302 travels with mobile devices 308 and 309. Mobile device 308 may be similar to mobile device 108 described previously, wherein mobile device 308 may include a first set of subsystems and be configured according to the framework of mobile device 200 of FIG. 2. Mobile device 308 may be a master device (e.g., a smart-phone) and include a controller such as controller 211 (not shown in this view). Mobile device 309 may be similar to mobile device 109. Mobile device 309 may include a second set of subsystems. Mobile device 309 may be a slave device in exemplary aspects and may include different and in some cases, a reduced set of subsystems in comparison to the master device or mobile device 308. Mobile device 309 may be a smartwatch or other wearable electronic device on the person of user 302. Mobile devices 308 and 309 may be in communication with one another based on any wired or wireless technology.

As shown, user 302 may wish to move from a current location inside an indoor structure 310 (e.g., an office building, a shopping mall, etc.) to an outdoor location. Note the terms "position" and "location" are used interchangeably herein. The user's intention to travel outside of the indoor structure 310 may be communicated via a user interface, similar to the user interface module 250, etc., of the example mobile device 200 depicted in relation to FIG. 2. For example, the user may provide text-data, voice data, etc., to an application program that receives that user information indicative of the user's intended destination location. The destination location may be specified as a name of a place, a point on a map (displayed on the mobile device's screen), an address, geographical coordinates, etc. In some embodiments, the starting location may be assumed to be the user's current location, as may be determined by a position determination procedure which can be implemented on either or both of mobile devices 308 and 309, or remotely at a remote server or remote computing device, such as a remote server 312 depicted in FIG. 3. Alternatively, in some embodiments, the starting location may be specified as a name of a place (provided by the user through a voice-interface, a keypad, or some other interface), a point on a map (displayed on the mobile device's screen), an address, geographical coordinates, etc. While located in an indoor environment, satellite signals may be restricted or unavailable and the location of the mobile devices 308 and 309 may be determined from signals received from one or more wireless access points. In the example of FIG. 3, one or both of mobile devices 308 and 309 may be in communication with access points 306a, 306b and 306c (e.g., WiFi-based access points, Bluetooth transceivers, cellular access points, etc.). Access points 306a-c may also be in communication with the remote server 312 (which may be directly coupled to the access points, or, as depicted in FIG. 3, may communicate with those access points wirelessly via transceiver/access point 314).

In some aspects, location of the mobile devices 308 and/or 309 may be determined based on such metrics as, for example, RSSI and/or RTT, determined by the corresponding mobile device. Generally, the determined RSSI and/or the RTT, corresponding to measurements of signals received from one or more access points can be used to determine an estimate of the device's location. For example, a database containing geographic locations, power profiles and RTTs for multiple access points with known geographical positions may be compared to currently determined RSSI and/or RTT values. Using these known positions, the relative distances of the mobile device 308 and/or 309 to the access points may be determined, and a geographic location of the mobile devices may be computed/derived (e.g., using multi-lateration procedures, such as a trilateration procedure). Other known methods and techniques for determining the current location of mobile devices 308 and 309 may also be used.

Based on the determined current location of the mobile device 308 and/or 309, and a selected destination location, a route of travel, such as route of travel 320 shown in FIG. 3, to be traversed by user 302 (and by extension, by the mobile devices 308 and 309 the user is carrying) is determined, either by a process implemented by one or both of mobile devices 308 and 309, or by a process implemented by a remote server. In either situation, at least one route of travel 320 for user 302 from the current location to the destination point is determined.

Based on the determined route of travel 320, a set of activities that are to be performed along the route of travel may be generated. The set of activities may be determined by controller 211 located on mobile device 308 in one illustrative example. The set of activities may alternatively be determined by a remote server, such as the remote server 312, and provided to mobile device 308.

In determining the set of activities, specific points along route of travel 320 may be identified. These points may include points corresponding to geographic locations where changes in the environments in which the mobile devices 308 and 309 are traveling are expected. These environment changes include changes in the operational environment, which may include changes to the communication capabilities available in the changing operational environments, and/or changes to the actual geographic environment, such as transitioning from an indoor environment to an outdoor environment. At least a portion of the set of activities may be need to be performed, and thus, assigned to mobile devices 308 and 309, based on a determination that at least one of mobile devices 308 or 309 is positioned at or within a threshold distance of a specific point on the route of travel. Moreover, in some cases, at least a portion of the set of activities is only performed while the route of travel is followed. As will be discussed in following sections, deviations from an original or pre-planned route of travel may result in a new or revised set of activities to be performed based on a new route of travel caused by the deviation.

In the example illustration of FIG. 3, four (4) points are shown, namely, points A, B, C, and D. Points A, B, C, D, may be expected transition points where the mobile devices 308 and 309 may move into a different geographical environment and/or to a new operation environment. Accordingly, one or more activities may be associated with these transition points, where the activities may need to be performed when at least one of the mobile devices 308/309 is within a predefined threshold distance from at least one of these points.

For example, point A is a point preceding the point where user 302 (and thus the mobile devices 308 and 309) will move from the top floor of the indoor structure 310 to the middle floor. Controller 211 may assign and/or schedule a set of activities collaboratively on mobile devices 308 and 309 along route of travel 320 from the current location to point A, and in some cases, specifically at point A. These activities may be performed by one or more subsystems located on mobile devices 308 and 309. However, there may be redundancy if both of the mobile devices 308 and 309 are performing same or similar activities to obtain same or similar results at point A. In order to avoid this redundant wastage of power and improve performance, controller 211 may distribute the activities at point A among the two sets of subsystems on mobile devices 308 and 309 respectively.

For example, an activity related to obtaining a floor map for the middle floor of the indoor structure 310 may be identified by controller 211 at point A. Rather than have both mobile devices 308 and 309 perform this activity, controller 211 may assign or schedule this activity to be performed only at mobile device 308 and deactivate any related subsystems which may have been used by mobile device 309 to obtain an updated floor map. Similarly, additional activities at point A may relate to activation of a plurality of sensors, receivers, monitors, etc. For example, pressure sensors may not be needed if the route stays on the same level, such as the top floor. However, at point A, pressure sensors may need to be activated. Controller 211 may activate the pressure sensors on mobile device 309 while keeping those on mobile device 308 deactivated, at point A, so that mobile device 308 may expend its power on other activities or conserve battery life. Moreover, collaborative performance of the activity may be possible, where mobile device 308 may altogether lack pressure sensors, but mobile device 309 may have pressure sensors. Thus, the functions of mobile device 308 may be enhanced by the use of pressure sensor data obtained from mobile device 309. In a different example, GNSS receivers may remain deactivated on both mobile devices 308 and 309 as long as point A falls inside indoor structure 310, even if point A is close to a window or exit with strong satellite signals being present. In other examples, controller 211 may identify activities related to monitoring biometric information of user 302 at point A where a change of elevation will occur. Controller 211 may assign these activities or schedule them to be performed on mobile device 309 by activating corresponding sensors and monitors on mobile device 309. Mobile device 309, which may be a smart-watch worn by user 302 on his/her wrist, may be better equipped to obtain measurements related to pulse rate of user 302, and as such, these activities may be assigned to or scheduled on mobile device 309.

In a similar manner to the determination of and managing of activities for point A, by controller 211, activities may be determined for points B, C, and D, as well as, for additional points in between these specifically identified points. Point B is similar to point A and represents a transition from the middle floor to the bottom floor of indoor structure 310. Similar functions as those described above for point A, may be performed by controller 211 at point B. Point C corresponds to a location where user 302 is about to transition from an indoor environment to an outdoor environment. At point C, controller 211 may identify activities related to requesting and/or computing signal acquisition assistance data (satellite positioning assistance data), activating a satellite receiver such as GNSS receiver 208 of mobile device 200 of FIG. 2, obtaining assistance data (e.g., map data) for the outdoor area, etc. Controller 211 may manage these activities to be collaboratively performed by mobile devices 308 and 309. For example, at point C, mobile device 308 may be better suited for performing the above-identified activities and thus, any subsystems on mobile device 309 which may be capable of performing these activities may be powered down. The assistance data, once procured by mobile device 308, may be shared with mobile device 309, for example.

Controller 211 may also identify activities to be performed when user 302 transitions to an outdoor area and reaches point D. These activities may include, for example, activating the acquiring satellite signals, deactivating any sensor that may have been needed while the mobile devices 308 and 309 were traveling indoor (e.g., a pressure sensor or altimeter which may have been operating to enable determination of the altitude of the mobile device), etc. Controller 211 may suitably schedule activation and/or deactivation of subsystems in mobile devices 308 and 309 for the performance of these activities at point D.

Sometimes there may be deviations or changes from predicted or pre-planned conditions for user 302. Controller 211 may be configured to be responsive to these changes and dynamically alter the list of activities to be performed and/or allocation of activities among the subsystems of mobile device 308 and 309. Such deviations or changes may be with regard to a pre-planned route of travel and/or conditions associated with one or more of mobile devices 308, 309, etc. Some of the potential changes in conditions which may happen and the ways in which controller 211 may respond to these changes will be discussed below.

As noted, in some aspects, the changes can be in terms of deviations from a pre-planned route of travel. The deviations may be in terms of diverging from an original path and/or changes in conditions such as environmental changes, changes in speed/velocity etc., which may occur or take place along the path. For example, user 302 may take a path which diverges from the pre-planned route of travel 320 discussed above. Additionally, or alternatively, there may be environmental changes (e.g., rain, storm, clouds, etc.) which can affect positioning functions due to changes or degradation in the signals used for multi-lateration of mobile devices 308/

309, for example. In some cases, a deviation from the pre-planned route of travel may introduce tunnels or other structures which can affect the signals used for multi-lateration of mobile devices 308/309 in the new route of travel. In some cases, there may be changes in speed/velocity of travel along route of travel 320, where user 302 may go faster/slower than expected, which can also affect the positioning functions.

Controller 211 may be configured to adapt or respond to these unexpected changes related to route of travel in several ways. For example, if the change incurs an alternative path, controller 211 may dynamically modify an originally generated list of activities and determine a new or revised set of activities associated with the new route of travel. Controller 211 may assign at least a portion of the new or revised set of activities among the subsystems of mobile device 308 and 309. Thus, a determination that a user deviated from the route of travel may result in activation or deactivation of one or more subsystems of mobile device 308 and/or 309. For example, if it is determined that user 302 has deviated from route of travel 320, one or more previously inactive transceivers may need to be activated to attempt to establish a communication link with an access point that may be closer to the present position of user 302. In aspects where signal losses may occur, controller 211 may switch or assign positioning functions to the device among mobile devices 308 and 309 which is likely to have stronger transceivers and or better capabilities for positioning functions under the diminished signal conditions. If controller 211 may become aware of upcoming signal degradations or losses (e.g., a new route of travel may involve passing through a tunnel, which the original route did not involve), controller 211 may modify a new set of activities which can, for example, turn off some transceivers in one or both of mobile devices 308, 309 in order to conserve battery life rather than needlessly search for and attempt to receive satellite signals which are unavailable or diminished. If there are unexpected changes in speed/velocity along a route of travel, controller 211 may modify the allocation of activities among mobile devices 308 and 309 based on which one of the devices would be better suited to handle positioning functions at the altered speed/velocity. Controller 211 may correspondingly manage the changes in allocation of activities as well as activations/deactivations of the subsystems on mobile devices 308 and 309 based on the new or revised set of activities resulting from the various changes related to a route of travel.

Some changes may also take place which are not necessarily related to the route of travel. For example, there may be changes in conditions of mobile devices 308, 309 related to battery life, state of charging, temporary activation/deactivation (e.g., one or both devices may be in a sleep mode), level of activity (e.g., highly active/busy, less active and available to accept new activities), etc. In some cases, one or more new devices may also become available and/or one or more existing devices may no longer be available, and/or detected/detectable by controller 211. Controller 211 may be configured to dynamically create a new set of activities and/or modify an existing set of activities and allocate/re-allocate these among available mobile devices in such cases. For example, based on battery life, activity levels, availability, etc., of mobile devices 308 and 309, controller 211 may activate/deactivate subsystems of one or both devices. In other examples, determining sets of activities and time, durations, or schedules related to these activities may also include other aspects of mobile devices 308 and 309, such as sensor calibration activities, device maintenance and updating operations, etc., which may need to be performed every certain time period, whether or not the mobile devices have arrived at some pre-specified location where location-based or route-based activities as discussed above are to be performed. In some cases, controller 211 may also take into account the battery lives of mobile devices 308 and 309. Mobile device 309 may, for example, communicate the status of its battery or charge levels running low to controller 211, whereby controller 211 may revise any previously scheduled activities on mobile device 309 (e.g., revise the time of start/stop, duration of the activity, etc.,) and/or transfer the scheduled activities on mobile device 309 to mobile device 308 (assuming mobile device 308 has sufficient battery life to handle the increase load for performing the transferred activities). Thus, in some aspects, scheduling these additional activities or revised activities can occur at various points of a user's route of travel and/or at various points of time during the travel, but these activities may not be directly related to a location or point in the route.

In order to be responsive to the various changes noted above, controller 211 may include functionality to detect changes in pre-planned conditions (which may or may not be specific to a route of travel) and to adapt to these changes by generating a new set of activities and/or revising an original set of activities. Controller 211 may include the functionality to manage and assign the new and/or revised set of activities among the two or more collocated mobile devices such as mobile devices 308 and 309 discussed above. Modules 502, 503, 504, and 506 shown in FIG. 5 and discussed further below may include such functionality.

It will be appreciated that embodiments include various methods for performing the processes, functions and/or algorithms disclosed herein. For example, in FIG. 4, an exemplary aspect can include a method 400 for use in managing activities among two or more collocated mobile devices is shown. At Block 402, the method includes determining a route of travel (e.g., 320) corresponding to the two or more collocated mobile devices (e.g., 308, 309) prior to a start of travel. As described previously, at least one of the two or more mobile devices (308 or 309) may receive from user 302 (e.g., via an input interface such as 250, 252, 254, 256, etc., of FIG. 2) information indicating the user's desired destination (e.g., the user may provide a pinpoint location of the destination on a map displayed on the mobile device's screen, or he/she may provide an address or specify a name of a place, etc.) The destination location and a starting point location (which may be the user's current location as determined through a multi-lateration processes, profile matching techniques, etc.) may then be used to determine, based on assistance data (including, e.g., map data, which may be stored at the local device, or at a remote server to which the current and destination location have been communicated) one or more possible routes from the current location to the destination. As noted, the route determination may be performed at a server or a remote computing device (e.g., remote server 312) in communication with at least one of the two or more collocated mobile devices (e.g., through access point 314) and/or at one of the two or more collocated mobile devices. Where more than one possible route of travel is available, the route that best meets some criterion (e.g., shortest or fastest route) may be the route selected.

Figure 4:
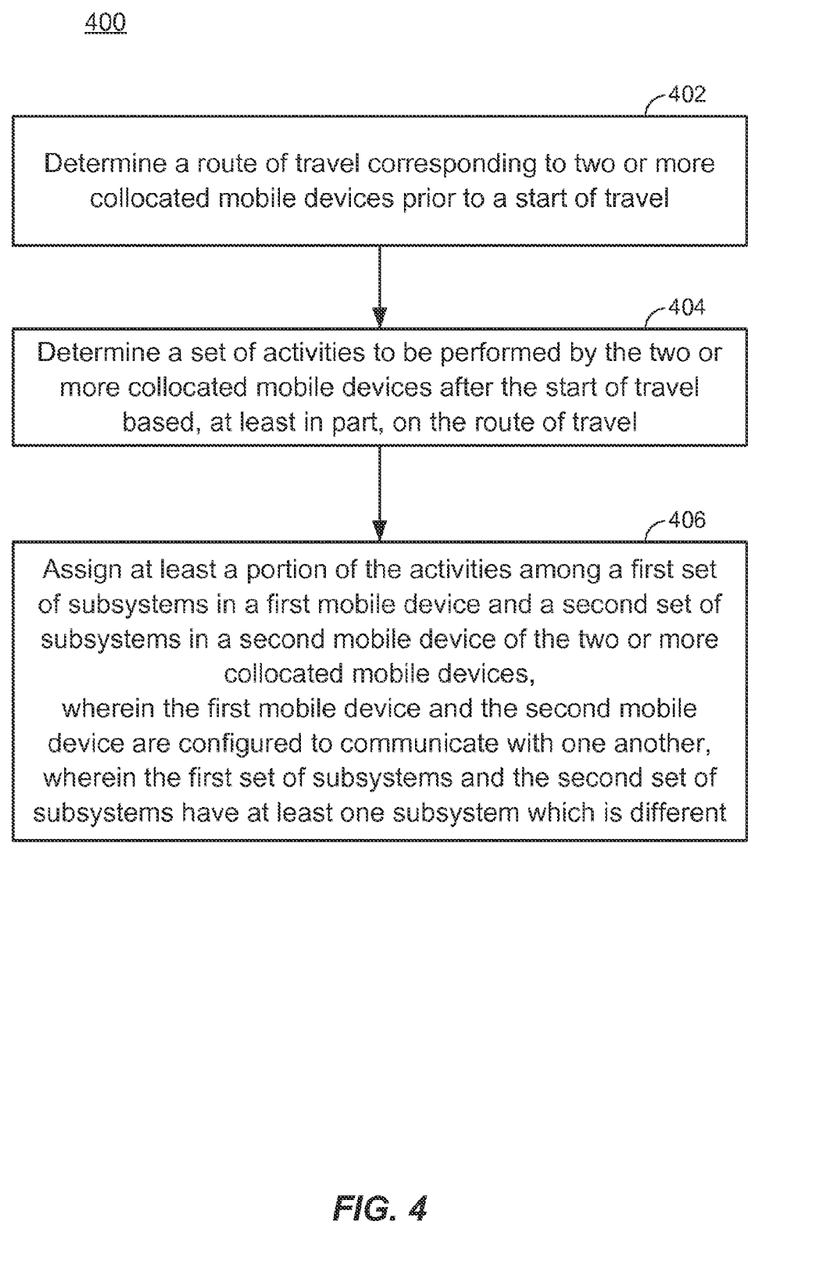
FIG. 4 is a flowchart of an example procedure to manage particular activities that may be performed by two or more mobile devices, for example as in FIG. 1, in accordance with certain example implementations.

At Block 404, the method 400 includes determining a set of activities to be performed by the two or more collocated mobile devices after the start of travel based, at least in part, on the route of travel. In more detail, based on the route of travel determined at Block 402, a set of activities (including positioning activities, biometric activities, device maintenance activities, etc.) associated with the route of travel. In some aspects, the set of activities is obtained by identifying points along the route where various activities may need to be performed. The identified points may include points where, for example, the user will transition from one geographical and/or operational environment to another geographic and/or operational environment. Changes to operational environments in which the user is traveling may include, for example, changes to the communication capabilities available in the changing operational environments, and changes to the actual geographic environment may include transitioning from an indoor environment to an outdoor environment, for example. If there are changes related to the route of travel and/or conditions associated with at least one of the two or more collocated devices, a new or revised set of activities are determined based on these changes.

At Block 406, the method 400 includes assigning at least a portion of the activities (either an original set of activities or a new/revised set of activities as the case may be) among a first set of subsystems in a first mobile device (e.g., mobile device 308) and a second set of subsystems in a second mobile device (e.g., mobile device 309), wherein the first mobile device and the second mobile device are configured to communicate with one another, wherein the first set and the second set have at least one subsystem which is different. For example, in accordance with the determined set of activities, one or more of the activities may be scheduled on subsystems of mobile device 308 (e.g., a smart-phone or a master device) and subsystems of mobile device 309 (e.g., a smart-watch or a slave device). The two mobile devices may have at least one different subsystem. For example, mobile device 308 may not have a pressure sensor whereas mobile device 309 may have a pressure sensor. In another example, mobile device 309 may not have a processor of the same caliber or performance level as a processor in mobile device 308. The two mobile devices may also have different receivers, sensors, antennae, input/output devices, configurations, capabilities, etc. Thus, a controller such as controller 211 may schedule activities among mobile devices 308 and 309 based on each device's capabilities, the requirements for a specific task, and additional considerations such as each device's battery levels. Exemplary navigation activities to be scheduled among the two mobile devices may relate to controlling the activation of one or more units (e.g., sensors, receivers, transceivers, other modules), obtaining assistance data, obtaining (e.g., computing) signal acquisition assistance data to facilitate satellite signal acquisition, establishing a communication link with an access point, controlling the activation of a device's one or more positioning modes, etc., when the mobile devices are about to transition from an indoor environment to an outdoor environment. Exemplary activities related to biometric functions may include activating/deactivating monitors, sensors, etc., for obtaining a user's biometric state based on when the mobile devices transition through changes in elevation, transition from indoor to outdoor environments, etc.

Figure 5:
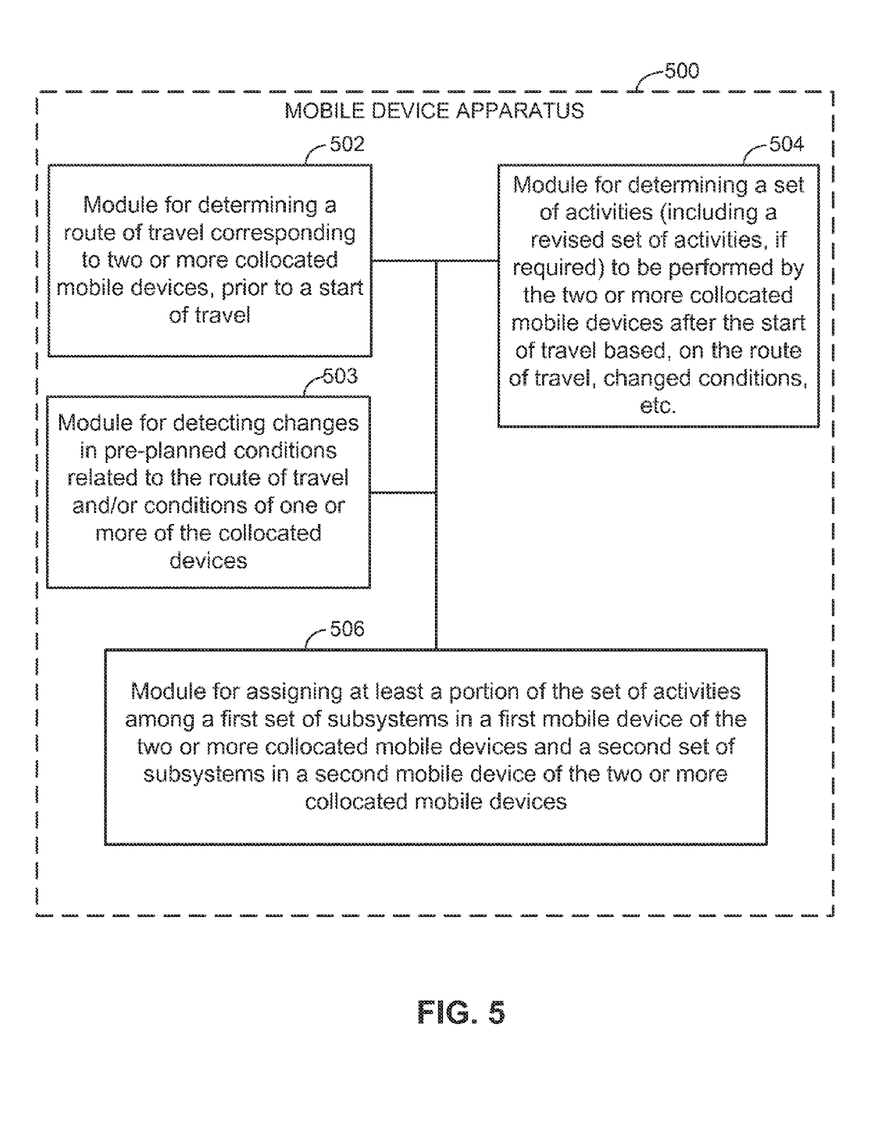
FIG. 5 is a simplified block diagram of sample aspects of an apparatus configured to support certain techniques as taught herein, in accordance with certain example implementations.

FIG. 5 illustrates an example mobile device apparatus 500 represented as a series of interrelated functional modules. Module 502 may include functionality for determining a route of travel corresponding to two or more collocated mobile devices (which may include mobile device apparatus 500 and one or more other mobile devices collocated with mobile device apparatus 500), prior to a start of travel. Module 502 may correspond at least in some aspects to, for example, a processing system in conjunction with positioning data, such as processor 210 in conjunction with wireless-based positioning module 216 in FIG. 2, as discussed herein.

As previously mentioned, apparatus 500 may also include functional module 503, where module 503 may include functionality for detecting changes in pre-planned conditions related to the route of travel and/or conditions of one or more of the collocated devices. For example, module 503 may include functionality for detecting one or more changes associated with the route of travel, wherein the one or more changes include one or more of a new route of travel, changes in environmental conditions, or changes in speed or velocity along the route of travel. Module 503 may also include functionality for detecting changes in one or more conditions related to at least one of the two or more collocated mobile devices, wherein the conditions include one or more of battery level, activity level, or availability of the at least one of the two or more collocated mobile devices. Module 503 may also correspond at least in some aspects to, for example, a processing system in conjunction with positioning data, such as processor 210 in conjunction with wireless-based positioning module 216 in FIG. 2, as discussed herein.

Module 504 may include functionality for determining a set of activities (either an original set of activities based on information available from module 502 and/or a new or revised set of activities based on information available from module 503) to be performed by the two or more collocated mobile devices after the start of travel based, at least in part, on the route of travel. Module 504 may correspond at least in some aspects to, for example, a controller in conjunction with a processor, such as controller 211 in conjunction with processor 210 in FIG. 2, as discussed herein.

Module 506 for assigning at least a portion of the set of activities (e.g., the original set of activities and/or the new or revised set of activities) among a first set of subsystems in a first mobile device of the two or more mobile devices and a second set of subsystems in a second mobile device of the two or more mobile devices, may correspond at least in some aspects to, for example, a controller in conjunction with a processor, such as controller 211 in conjunction with processor 210 in FIG. 2, as discussed herein.

Additionally, in some instances, one or more of modules 502, 503, 504, and/or 506 may correspond at least in some aspects to all or part of communication interface 203 in FIG. 2. In certain instances, e.g., as part of an act of assigning activities and/or thereafter as part of the communication between the various devices, one or more signals may transmitted to at least one of the two or more collocated mobile devices. A processor, for example, processor 210 of FIG. 2, may be configured to initiate transmission of the one or more signals to at least one of the two or more collocated mobile devices. The transmitted signals may be indicative of at least one activity that may be assigned to at least one recipient mobile device among the collocated mobile devices. In certain instances, one or more activities may be conditional. For example, one or more activities may be performed based on a determination that at least one of the collocated mobile devices is estimated to be positioned within a threshold distance of a point on the route of travel. In certain instances, some activities may only be performed while a particular route of travel is determined to have been followed or is being followed.

The functionality of the modules of FIG. 5 may be implemented in various ways consistent with the teachings herein. In some designs, the functionality of these modules may be implemented as one or more electrical components. In some designs, the functionality of these blocks may be implemented as a processing system including one or more processor components. In some designs, the functionality of these modules may be implemented using, for example, at least a portion of one or more integrated circuits (e.g., an ASIC). As discussed herein, an integrated circuit may include a processor, software, other related components, or some combination thereof. Thus, the functionality of different modules may be implemented, for example, as different subsets of an integrated circuit, as different subsets of a set of software modules, or a combination thereof. Also, it will be appreciated that a given subset (e.g., of an integrated circuit and/or of a set of software modules) may provide at least a portion of the functionality for more than one module.

In addition, the components and functions represented by FIG. 5, as well as other components and functions described herein, may be implemented using any suitable means. Such means also may be implemented, at least in part, using corresponding structure as taught herein. For example, the components described above in conjunction with the "module for" components of FIG. 5 also may correspond to similarly designated "means for" functionality. Thus, in some aspects one or more of such means may be implemented using one or more of processor components, integrated circuits, or other suitable structure as taught herein.

Those of skill in the art will appreciate that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Further, those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The methods, sequences and/or algorithms described in connection with the embodiments disclosed herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor.

Accordingly, an embodiment of the disclosure can include an article which can comprise non-transitory computer readable media having stored therein instructions that are executable by a processor to manage activities among two or more collocated mobile devices. Accordingly, the disclosure is not limited to illustrated examples and any means for performing the functionality described herein are included in embodiments of the disclosure.

While the foregoing disclosure shows illustrative embodiments of the disclosure, it should be noted that various changes and modifications could be made herein without departing from the scope of the disclosure as defined by the appended claims. The functions, steps and/or actions of the method claims in accordance with the embodiments of the disclosure described herein need not be performed in any particular order. Furthermore, although elements of the disclosure may be described or claimed in the singular, the plural is contemplated unless limitation to the singular is explicitly stated.

What is claimed is:

1. A method for use in managing activities among two or more collocated mobile devices, the method comprising:
   determining a route of travel corresponding to the two or more collocated mobile devices prior to a start of travel;
   determining a set of activities to be performed by the two or more collocated mobile devices after the start of travel based, at least in part, on the route of travel; and
   assigning at least a portion of the set of activities among a first set of subsystems in a first mobile device of the two or more collocated mobile devices and a second set of subsystems in a second mobile device of the two or more collocated mobile devices,
   wherein the first mobile device and the second mobile device are configured to communicate with one another, and wherein the first set of subsystems and the second set of subsystems have at least one subsystem which is different.

2. The method of claim 1, and further comprising: transmitting a signal to at least one of the two or more collocated mobile devices, the signal being indicative of at least one activity assigned to the at least one of the two or more collocated mobile devices.

3. The method of claim 1, wherein the assigning at least the portion of the set of activities comprises:
   disabling one or more subsystems in the first set of subsystems,
   disabling one or more subsystems in the second set of subsystems, or
   both.

4. The method of claim 1, wherein determining the route of travel, determining the set of activities, and assigning at least the portion of the set of activities are performed by the first mobile device.

5. The method of claim 1, wherein the first mobile device comprises a master device and the second mobile device comprises a slave device.

6. The method of claim 1, wherein determining the route of travel, determining the set of activities, and assigning at least the portion of the set of activities are performed by a remote computing device in communication with at least the first mobile device.

7. The method of claim 1, wherein the first mobile device comprises a mobile phone and the second mobile device comprises a wearable electronic device.

8. The method of claim 1, wherein at least one activity of the set of activities corresponds to a positioning function.

9. The method of claim 1, wherein at least one activity of the set of activities corresponds to a biometric function.

10. The method of claim 1 further comprising:
    detecting one or more changes associated with the route of travel, wherein the one or more changes include one or more of a new route of travel, changes in environmental conditions, or changes in speed or velocity along the route of travel;
    determining a new or revised set of activities associated with the one or more changes; and
    assigning at least a portion of the new or revised set of activities among the first set of subsystems in the first mobile device and the second set of subsystems in the second mobile device.

11. The method of claim 1 further comprising:
  detecting changes in one or more conditions related to at least one of the two or more collocated mobile devices, wherein the conditions include one or more of battery level, activity level, or availability of the at least one of the two or more collocated mobile devices;
  determining a new or revised set of activities associated with the detected changes in the one or more conditions; and
  assigning at least a portion of the new or revised set of activities among the first set of subsystems in the first mobile device and the second set of subsystems in the second mobile device.

12. The method of claim 1, and further comprising:
  performing at least one activity from at least the portion of the set of activities based on a determination that at least one of the two or more collocated mobile devices is positioned within a threshold distance of a point on the route of travel.

13. The method of claim 1, wherein at least one of the two or more collocated mobile devices is located on a user's person.

14. An apparatus configured to manage activities among two or more collocated mobile devices, the apparatus comprising:
  memory; and
  a processor coupled to the memory and configured to:
    determine a route of travel corresponding to the two or more collocated mobile devices prior to a start of travel;
    determine a set of activities to be performed by the two or more collocated mobile devices after the start of travel based, at least in part, on the route of travel; and
    assign at least a portion of the set of activities among a first set of subsystems in a first mobile device of the two or more collocated mobile devices and a second set of subsystems in a second mobile device of the two or more collocated mobile devices,
    wherein the first mobile device and the second mobile device are configured to communicate with one another, and wherein the first set of subsystems and the second set of subsystems have at least one subsystem which is different.

15. The apparatus of claim 14, wherein the processor is further configured to initiate transmission of a signal to at least one of the collocated mobile devices, the signal being indicative of at least one activity assigned to the at least one of the collocated mobile devices.

16. The apparatus of claim 14, wherein the processor is further configured to:
  disable one or more subsystems in the first set of subsystems,
  disable one or more subsystems in the second set of subsystems, or
  both.

17. The apparatus of claim 14, wherein the apparatus is provisioned within the first mobile device.

18. The apparatus of claim 14, wherein at least one of the two or more collocated mobile devices is located on a user's person.

19. The apparatus of claim 14, wherein the apparatus comprises a remote computing device in communication with at least the first mobile device.

20. The apparatus of claim 14, wherein the first mobile device comprises a mobile phone and the second mobile device comprises a wearable electronic device.

21. The apparatus of claim 14, wherein at least one activity of the set of activities corresponds to a positioning function.

22. The apparatus of claim 14, wherein at least one activity of the set of activities corresponds to a biometric function.

23. The apparatus of claim 14, wherein the processor is further configured to:
  detect one or more changes associated with the route of travel, wherein the one or more changes include one or more of a new route of travel, changes in environmental conditions, or changes in speed or velocity along the route of travel;
  determine a new or revised set of activities associated with the one or more detected changes; and
  assign at least a portion of the new or revised set of activities among the first set of subsystems in the first mobile device and the second set of subsystems in the second mobile device.

24. The apparatus of claim 14, wherein the processor is further configured to:
  detect changes in one or more conditions related to at least one of the two or more collocated mobile devices, wherein the conditions include one or more of battery level, activity level, or availability of the at least one of the two or more collocated mobile devices;
  determine a new or revised set of activities associated with the detected changes in the one or more conditions; and
  assign at least a portion of the new or revised set of activities among the first set of subsystems in the first mobile device and the second set of subsystems in the second mobile device.

25. The apparatus of claim 14, wherein the processor is further configured to:
  perform at least one activity from at least the portion of the set of activities based on a determination that at least one of the collocated mobile devices is positioned within a threshold distance of a point on the route of travel.

26. A system for managing activities among two or more collocated mobile devices, the system comprising:
  means for determining a route of travel corresponding to the two or more collocated mobile devices prior to a start of travel;
  means for determining a set of activities to be performed by the two or more collocated mobile devices after the start of travel based, at least in part, on the route of travel; and
  means for assigning at least a portion of the set of activities among a first set of subsystems in a first mobile device of the two or more collocated mobile devices and a second set of subsystems in a second mobile device of the two or more collocated mobile devices,
  wherein the first mobile device and the second mobile device are configured to communicate with one another, and wherein the first set of subsystems and the second set of subsystems have at least one subsystem which is different.

27. The apparatus of claim 26, further comprising:
  means for transmitting a signal to at least one of the collocated mobile devices, the signal being indicative of at least one activity assigned to the at least one of the collocated mobile devices.

28. The apparatus of claim 26, wherein the apparatus is provisioned, at least in part, within at least one of the two or more collocated mobile devices.

29. An article for use in managing activities among two or more collocated mobile devices, the article comprising:
  a non-transitory computer-readable storage medium having stored therein instructions that are executable by a processor to:

determine a route of travel corresponding to the two or more collocated mobile devices prior to a start of travel;

determine a set of activities to be performed by the two or more collocated mobile devices after the start of travel based, at least in part, on the route of travel; and assign at least a portion of the set of activities among a first set of subsystems in a first mobile device of the two or more collocated mobile devices and a second set of subsystems in a second mobile device of the two or more collocated mobile devices, wherein the first mobile device and the second mobile device are configured to communicate with one another, and wherein the first set of subsystems and the second set of subsystems have at least one subsystem which is different.

30. The article of claim 29, wherein the instructions are further executable by the processor to:

initiate transmission of a signal to at least one of the collocated mobile devices, the signal being indicative of at least one activity assigned to the at least one of the collocated mobile devices.

\* \* \* \* \*